US012672654B2

(12) United States Patent
Schoenfelder et al.

(10) Patent No.: US 12,672,654 B2
(45) Date of Patent: Jul. 7, 2026

(54) METHOD FOR CONTROLLING MICROBIAL GROWTH IN SUGAR PROCESSING

(71) Applicant: HYDRITE CHEMICAL CO., Brookfield, WI (US)

(72) Inventors: Carl Schoenfelder, Lakeville, MN (US); Scott K. Cumming, Sun Prairie, WI (US)

(73) Assignee: HYDRITE CHEMICAL CO., Brookfield, WI (US)

( * ) Notice: Subject to any disclaimer, the term of this patent is extended or adjusted under 35 U.S.C. 154(b) by 581 days.

(21) Appl. No.: 18/017,885

(22) PCT Filed: Jul. 30, 2021

(86) PCT No.: PCT/US2021/043995
§ 371 (c)(1),
(2) Date: Jan. 25, 2023

(87) PCT Pub. No.: WO2022/081236
PCT Pub. Date: Apr. 21, 2022

(65) Prior Publication Data
US 2023/0270108 A1     Aug. 31, 2023

Related U.S. Application Data

(60) Provisional application No. 63/059,741, filed on Jul. 31, 2020.

(51) Int. Cl.
*A61L 2/00*          (2006.01)
*A01N 37/16*       (2006.01)
(Continued)

(52) U.S. Cl.
CPC ................ *A01N 37/16* (2013.01); *A01P 1/00* (2021.08); *G01N 33/182* (2013.01)

(58) Field of Classification Search
CPC ........ A01N 59/00; A01N 37/16; A01N 43/16; B65B 31/04; A61L 2/186; A61L 2/24; A23B 7/157; C13B 10/006
(Continued)

(56) References Cited

U.S. PATENT DOCUMENTS 2,165,348 A     7/1939   Daley
2,560,125 A     7/1951   Pearson
(Continued)

FOREIGN PATENT DOCUMENTS

EP          0678123 B1     4/1997
EP          0943692 B1     10/2003
(Continued)

OTHER PUBLICATIONS

International Search Report and Written Opinion dated Jun. 24, 2022 in connection with PCT/US21/43995, 20 pgs.
(Continued)

*Primary Examiner* — Monzer R Chorbaji
(74) *Attorney, Agent, or Firm* — Quarles & Brady LLP

(57) ABSTRACT

A method for controlling microbial growth in a sugar processing system is disclosed, wherein the method comprises adding a peroxy acid into water of a flume system used for transporting a sugar-containing plant material from a delivery or storage location to a wash system. In one non-limiting example embodiment, the sugar-containing plant material comprises sugar beets, and the peroxy acid comprises peracetic acid.

19 Claims, 2 Drawing Sheets

(51) Int. Cl.

| | | |
|---|---|---|
| *A01N 39/00* | (2006.01) |
| *A01P 1/00* | (2006.01) |
| *A21D 4/00* | (2006.01) |
| *A61L 9/00* | (2006.01) |
| *G01N 33/18* | (2006.01) |

(58) Field of Classification Search

USPC ............ 422/1, 28, 32, 34; 424/616; 426/331

See application file for complete search history.

(56) References Cited

U.S. PATENT DOCUMENTS

| | | | |
|---|---|---|---|
| 2,586,846 | A | 2/1952 | McNerny et al. |
| 4,451,489 | A | 5/1984 | Beale et al. |
| 6,197,784 | B1 | 3/2001 | Fuchs et al. |
| 6,656,287 | B2 | 12/2003 | Sanders |
| 8,277,733 | B2 | 10/2012 | McSherry et al. |
| 9,551,043 | B2 | 1/2017 | Van Haute et al. |
| 10,081,561 | B2 | 9/2018 | Champion et al. |
| 2001/0054420 | A1 | 12/2001 | Reisig et al. |
| 2006/0121126 | A1 | 6/2006 | McFadden et al. |
| 2009/0324790 | A1 † | 12/2009 | Hilgren |
| 2010/0075006 | A1 | 3/2010 | Semenza |
| 2010/0108092 | A1 | 5/2010 | Zaharis |
| 2015/0159230 | A1 | 6/2015 | Van Haute et al. |
| 2016/0106096 | A1 | 4/2016 | Hilgren et al. |
| 2020/0172988 | A1 | 6/2020 | Burchtorf et al. |
| 2021/0238070 | A1 † | 8/2021 | Burchtorf |

FOREIGN PATENT DOCUMENTS

| | | | | | |
|---|---|---|---|---|---|
| EP | 1138787 | B1 | | 9/2005 | |
| EP | 1837409 | A1 | | 9/2007 | |
| EP | 1837409 | B1 | * | 9/2009 | .......... C13B 10/006 |
| WO | 1994016110 | A1 | | 7/1994 | |
| WO | 2001014594 | A2 | | 3/2001 | |
| WO | 2013160546 | A1 | | 10/2013 | |
| WO | 2019046574 | A1 | | 3/2019 | |
| WO | 2019125917 | A1 | | 6/2019 | |
| WO | 2022/081236 | A2 | | 4/2022 | |

OTHER PUBLICATIONS

Disinfectants Peracetic Acid, Retrieved from https://www.lenntech.com/processes/disinfection/chemical/disinfectants-peracetic-acid.htm, Copyright 1998-2024 Lenntech B.V., 2 pages.

Larson et al., Recent Developments in Beet Transport Water Management, Nalco Chemical Company, 1993, 132-141.

Peracetic Acid Handling/Processing, Technical Evaluation Report, OMRI for the USDA National Organic Program, 2016.

Volpe, Development of Measurement Methods for Testing of Hydrokinetic Devices to Evaluate the Environmental Effect on Local Substrate, Honors Theses: Bucknell University, Retrieved from https://digitalcommons.bucknell.edu/honors_theses/16, 2011, 75 pages.

Machine translation of EP 0943692 B1 dated Oct. 15, 2003.

Machine translation of EP 1138787 B1 dated Sep. 28, 2005.

European, XP 1837409 A1, Sep. 25, 2007, Nalco Italiana S.R.L.†

\* cited by examiner

† cited by third party

METHOD FOR CONTROLLING MICROBIAL GROWTH IN SUGAR PROCESSING

CROSS-REFERENCES TO RELATED APPLICATIONS

This application is a 371 application of PCT International Application PCT/US2021/043995 filed Jul. 30, 2021, which claims priority to U.S. Patent Application No. 63/059,741 filed Jul. 31, 2020.

STATEMENT REGARDING FEDERALLY SPONSORED RESEARCH

Not Applicable.

BACKGROUND OF THE INVENTION

1. Field of the Invention

The invention relates to methods for controlling microbial growth in sugar processing.

2. Description of the Related Art

Sugar (sucrose) is primarily obtained from plant raw materials, such as sugar beets and sugar cane, by cutting the raw materials and extracting sugar-containing solutions from the plant parts. Sugar beets are subject to microbiological decay through bacteria, yeasts, and fungi within certain pH values. There is a risk of infestation by microorganisms during sugar processing. Microorganisms can degrade sugars contained in the raw materials and process materials to acids and gases to cause loss of sugar product, and/or cause elevated bacterial populations in the products. Microorganisms can influence the process negatively, not only by causing sugar losses, but also, for example, by causing pH drops and high lactic acid concentrations, which can affect other steps in the process.

A typical sugar beet processing operation includes a flume water system that is used to transport the beets from a post-harvest delivery or storage location into the factory beet washer while simultaneously removing field dirt that might adversely affect cutting and extraction. Acid production is a natural, continuous process in flume water due to acid-forming bacteria activity. To maintain an acceptable microbial count, a common method of flume water treatment is to maintain the pH in the alkaline range using lime. Maintaining this high pH controls acid forming bacterial activity.

Historic industry best practice regarding flume system water microbial management is to drive pH up to a range of 10.5 pH or above. This strategy is primarily driven by the rationale that a wide variety of bacteria species struggle to survive at such a high pH. By suppressing microbial activity in the flume, sugar recovery improves through the process.

The recognitions and detractions of this strategy using lime include:

i. The lime kiln and/or lime delivery system to the flume system must be robust, with adequate capacity for this strategy to be effective and efficient.

ii. There is a high relative cost with hydrated/pebble lime if/when kiln capacity cannot support flume water lime addition. Costs become greater in feeder systems where the pebble lime is not fully dissolved.

iii. If pH decreases below a certain point, an inordinate amount of lime is required to reach or regain the high pH, at high input costs.

iv. Hard calcium scale develops repeatedly over time, blinding screens and other equipment, typically resulting in a deliberate manipulation of flume system pH downward. While pH is suppressed to break down scale, bacteria takes hold which contribute to sugar losses, and once again, an inordinate amount of lime is required to regain control.

v. Inter-campaign maintenance costs associated with flume system de-scaling can be high.

Sugar processing plants that do not have sufficient kiln capacity or necessary lime handling equipment to effectively maintain a high pH strategy have compounded issues associated with low pH (>4 but <10) flume water, such as:

i. excessive lime is expended for limited, and sometimes negligible return on investment;

ii. accelerated flume system equipment corrosion occurs; and iii. high bacteria loading carrying forward to the process results in excessive sugar losses.

Thus, there exists a need for improved methods for controlling microbial growth in sugar processing.

SUMMARY OF THE INVENTION

Considering the primary reason to add lime to the flume system is to suppress microbe proliferation, and also considering the identified challenges associated with managing a high pH flume system, the present invention addresses the foregoing needs by providing improved methods for controlling microbial growth in sugar beet processing. The methods of the invention provide an alternative strategy that is more cost effective.

Sugar processing plants that do not have sufficient liming capacity and/or delivery systems find themselves either (1) not controlling pH or, (2) running relatively low pH, and therefore are viable candidates for the addition of a peroxy acid, such as peracetic acid (PAA), according to the present invention, to effectively control the bacteria as well as pH in the flume system.

Considering the natural pH range of the sugar beet is close to neutral and assuming the depression in flume system pH from that relative neutral position is due to the presence of significant lactic (or related) acids, flume system pH can be increased and furthermore controlled by the addition of a small amount of PAA.

While initially the concept of "adding an acid to increase pH" may be counter-intuitive, one must consider the significant (hundreds of parts per millions) presence of lactic acid being eliminated by a weaker acid (PAA), delivered in much lower concentration (at least ten-fold less). Testing has shown there could be a slight depression to the natural sugar beet and flume system water pH at the onset, but that depression will be relatively minimal (<0.5 pH) and the pH will stabilize instead of continuing to drop.

One version of the method of the invention uses a three-tiered approach as follows: (1) replace the current microbial growth inhibitor (lime) with a true biocide chemistry, i.e., a peroxy acid, such as peracetic acid (PAA); (2) employ genome testing to identify species type and concentration in the water of the flume system, thus allowing more precise and effective treatment; and (3) implement monitoring equipment, including but not limited to oxidation reduction potential (ORP), that validates the treatment schedule and provides for continuous chemical management/adjustment. Optionally, less than the entire amount of lime may be replaced with a true biocide chemistry, i.e., a peroxy acid, such as peracetic acid.

Some advantages of the method of the invention include: (1) more effective management of bacteria through to the sugar extraction plant, by means of using a true biocide vs. relying on pH to suppress proliferation; (2) better control of agent (chemical pump vs. feeder or rotary air lock) and assurance 100% of product introduced to the flume system is available for utilization vs. pebble lime or similar; (3) more neutralized pH will avoid inter-campaign (or more frequent) scale removal costs; (4) more neutralized pH will avoid costs associated with accelerated corrosion; (5) inordinate costs associated with "spiking" lime addition to regain high pH after traditional de-scaling can be avoided; and (6) excessive and accelerated microbial proliferation while deliberately lowering the pH within the "lowering pH gap" with traditional de-scaling can be avoided.

Following a flume system survey, chemistry (e.g., a peroxy acid) can be introduced to the flume system within a designated section (e.g., immediately following the feeder wheel) by way of a metering pump and tote arrangement. Initial usage rates will likely be higher, and steadily reduce to a rate (e.g., <10 ppm) to control microbes and stabilize pH. Continuous feed may be implemented but has been found not to be required in all applications. The flume system water pH will gradually rise from about 4-4.9 to a range from upper 5 to high 6. The overall cost will be less than using lime, and recovery of sugar will improve. Optionally, additional peroxy acid can be added in a recycled water unit and/or water storage pond(s).

In one aspect, the invention provides a method for controlling microbial growth in a sugar processing system. The method comprises: (a) adding a peroxy acid into water of a flume system used for transporting a sugar-containing plant material from a delivery or storage location to a wash system. In one version of the method, the peroxy acid has a formula $R^1CO_3H$, where $R^1$ is selected from $C_1$ to $C_{18}$ alkyl. In one version of the method, the peroxy acid has a formula $R^1CO_3H$, where $R^1$ is selected from $C_1$ to $C_8$ alkyl. The peroxy acid can comprise peracetic acid. In one version of the method, a peroxide source is reacted with a carboxylic acid to form the peroxy acid. In one version of the method, the peroxide source is hydrogen peroxide, and the carboxylic acid is acetic acid. The peroxide source and the carboxylic acid can be reacted in the water of the flume system.

In one version of the method, the peroxy acid is added into the water of the flume system such that a concentration of the peroxy acid in the water of the flume system is in a range of 1 ppm to 2500 ppm. In one version of the method, the peroxy acid is added into the water of the flume system such that a pH in the water of the flume system is in a range of 2 to 12. In one version of the method, the peroxy acid is added into the water of the flume system such that a pH in the water of the flume system is in a range of 5.5 to 11. In one version of the method, the peroxy acid is added into the water of the flume system such that a pH in the water of the flume system is in a range of 5.5 to 6.9.

The method can further comprise: (b) determining a concentration of the peroxy acid in the water of the flume system; and (c) adding additional peroxy acid into the water of the flume system when the concentration falls below a predetermined value. The method can further comprise: (b) sensing a measurable physical property of the water of the flume system; (c) generating a physical property signal corresponding to the measurable physical property, the physical property signal correlating to a concentration of the peroxy acid in the water of the flume system; (d) transmitting the physical property signal to a controller; and (e) when the concentration falls below a predetermined value stored in the controller, providing a control signal from the controller to open a supply valve in fluid communication with a source of the peroxy acid and the flume system thereby adding additional peroxy acid into the water of the flume system. The measurable physical property can be selected from the group consisting of pH, conductivity, and oxidation reduction potential.

In one version of the method, the peroxy acid is added into the water of the flume system at a point after a beet feeder that is positioned between the delivery or storage location and a water channel of the flume system. In one version of the method, the peroxy acid is added into the water of the flume system as a 1% w/w to 35% w/w aqueous solution of the peroxy acid. In one version of the method, the peroxy acid is added into the water of the flume system as a 20% w/w to 30% w/w aqueous solution of the peroxy acid.

In one version of the method, the sugar-containing plant material is selected from sugar beet, sugar cane, maize, sorghum, carrots, coconuts, nectarines, pineapples, mangoes, jackfruit, peaches, cantaloupe, apricots, bananas, grapes, apples, pears, cherries, oranges, or any combination thereof. In one version of the method, the sugar-containing plant material is sugar beet.

In one version of the method, the method reduces bacteria count of bacteria that consume sugar. In one version of the method, the method increases yield of sugar from the sugar processing system. In one version of the method, the method reduces a count of insects in the water of the flume system. In one version of the method, step (a) comprises sampling the water of the flume system to determine a count of insects in the water of the flume system and adding the peroxy acid into the water of the flume system such that a concentration of the peroxy acid in the water of the flume system reduces the count of insects in the water of the flume system.

The method can further comprise: (b) adding additional peroxy acid into a recycled water unit that is in fluid communication with (i) a water storage pond and (ii) an outlet of the wash system or an outlet of the flume system. Step (b) can comprise adding additional peroxy acid into the recycled water unit such that a concentration of the additional peroxy acid in the water of the recycled water unit is in a range of 1 ppm to 2500 ppm. In one version of the method, step (b) comprises adding additional peroxy acid into the recycled water unit such that a pH in the water of the recycled water unit is in a range of 2 to 12. In one version of the method, step (b) comprises adding additional peroxy acid into the recycled water unit such that a pH in the water of the recycled water unit is in a range of 5.5 to 11. In one version of the method, the additional peroxy acid is added into the water of the recycled water unit as a 1% w/w to 35% w/w aqueous solution of the additional peroxy acid. In one version of the method, the additional peroxy acid is added into the water of the recycled water unit as a 20% w/w to 30% w/w aqueous solution of the additional peroxy acid.

The method can further comprise: (b) adding additional peroxy acid into a water storage pond that is in fluid communication with an inlet of the flume system. In one version of the method, the water storage pond is in fluid communication with a recycled water unit that is in fluid communication with an outlet of the wash system or an outlet of the flume system. In one version of the method, step (b) comprises adding additional peroxy acid into the water storage pond such that a concentration of the additional peroxy acid in the water of the water storage pond is in a range of 1 ppm to 2500 ppm. In one version of the method, step (b) comprises adding additional peroxy acid into the water storage pond such that a pH in the water of the water storage pond is in a range of 2 to 12. In one version of the method, step (b) comprises adding additional peroxy acid into the water storage pond such that a pH in the water of the recycled water unit is in a range of 5.5 to 11. In one version of the method, the additional peroxy acid is added into the water of the water storage pond as a 1% w/w to 35% w/w aqueous solution of the additional peroxy acid. In one version of the method, the additional peroxy acid is added into the water of the water storage pond as a 20% w/w to 30% w/w aqueous solution of the additional peroxy acid.

The method can further comprise adding additional peroxy acid into water of an extraction system of the sugar processing system. In one version of the method, the extraction system is in fluid communication with the flume system. In one version of the method, step (b) comprises adding additional peroxy acid into the water of the extraction system such that a concentration of the additional peroxy acid in the extraction system is in a range of 1 ppm to 2500 ppm. In one version of the method, step (b) comprises adding additional peroxy acid into the water of the extraction system such that a pH in the water of the extraction system is in a range of 2 to 12. In one version of the method, step (b) comprises adding additional peroxy acid into the water of the extraction system such that a pH in the water of the extraction system is in a range of 5.5 to 11. In one version of the method, the additional peroxy acid is added into the water of the extraction system as a 1% w/w to 35% w/w aqueous solution of the additional peroxy acid. In one version of the method, the additional peroxy acid is added into the water of the extraction system as a 20% w/w to 30% w/w aqueous solution of the additional peroxy acid.

In one version of the method, the additional peroxy acid has a formula $R^1CO_3H$, where $R^1$ is selected from $C_1$ to $C_{18}$ alkyl. In one version of the method, the additional peroxy acid has a formula $R^1CO_3H$, where $R^1$ is selected from $C_1$ to $C_8$ alkyl. In one version of the method, the additional peroxy acid comprises peracetic acid. In one version of the method, step (b) comprises reacting a peroxide source with a carboxylic acid to form the additional peroxy acid. In one version of the method, the peroxide source is hydrogen peroxide, and the carboxylic acid is acetic acid.

In another aspect, the invention provides a method for controlling microbial growth in a sugar processing system having a flume system used for transporting a sugar-containing plant material from a delivery or storage location to a wash system wherein lime is used in the flume system. The method comprises: (a) replacing at least a portion of the lime with a peroxy acid, wherein the peroxy acid is added into water of the flume system. In one version of the method, the peroxy acid has a formula $R^1CO_3H$, where $R^1$ is selected from $C_1$ to $C_{18}$ alkyl. In one version of the method, the peroxy acid has a formula $R^1CO_3H$, where $R^1$ is selected from $C_1$ to $C_8$ alkyl. In one version of the method, the peroxy acid comprises peracetic acid. In one version of the method, step (a) comprises reacting a peroxide source with a carboxylic acid to form the peroxy acid. In one version of the method, the peroxide source is hydrogen peroxide, and the carboxylic acid is acetic acid. In one version of the method, the peroxide source and the carboxylic acid are reacted in the water of the flume system.

In one version of the method, step (a) comprises adding the peroxy acid into the water of the flume system such that a concentration of the peroxy acid in the water of the flume system is in a range of 1 ppm to 2500 ppm. In one version of the method, step (a) comprises adding the peroxy acid into the water of the flume system such that a pH in the water of the flume system is in a range of 2 to 12. In one version of the method, step (a) comprises adding the peroxy acid into the water of the flume system such that a pH in the water of the flume system is in a range of 5.5 to 11. In one version of the method, step (a) comprises adding the peroxy acid into the water of the flume system such that a pH in the water of the flume system is in a range of 5.5 to 6.9. In one version of the method, step (a) comprises replacing all of the lime with the peroxy acid. The peroxy acid stabilizes a pH of the sugar processing system.

In another aspect, the invention provides a method for controlling microbial growth in a sugar processing system. The method comprises: (a) adding a peroxy acid into water of an extraction system of the sugar processing system, wherein the extraction system extracts sugar from a sugar-containing plant material. In one version of the method, the peroxy acid has a formula $R^1CO_3H$, where $R^1$ is selected from $C_1$ to $C_{18}$ alkyl. In one version of the method, the peroxy acid has a formula $R^1CO_3H$, where $R^1$ is selected from $C_1$ to $C_8$ alkyl. In one version of the method, the peroxy acid comprises peracetic acid. In one version of the method, step (a) comprises reacting a peroxide source with a carboxylic acid to form the peroxy acid. In one version of the method, the peroxide source is hydrogen peroxide, and the carboxylic acid is acetic acid. In one version of the method, the peroxide source and the carboxylic acid are reacted in the water of the extraction system.

In one version of the method, step (a) comprises adding the peroxy acid into the water of the extraction system such that a concentration of the peroxy acid in the water of the extraction system is in a range of 1 ppm to 2500 ppm. In one version of the method, step (a) comprises adding the peroxy acid into the water of the extraction system such that a pH in the water of the extraction system is in a range of 2 to 12. In one version of the method, step (a) comprises adding the peroxy acid into the water of the extraction system such that a pH in the water of the extraction system is in a range of 5.5 to 11. In one version of the method, step (a) comprises adding the peroxy acid into the water of the extraction system such that a pH in the water of the extraction system is in a range of 5.5 to 6.9. In one version of the method, the peroxy acid is added into the water of the extraction system as a 1% w/w to 35% w/w aqueous solution of the peroxy acid. In one version of the method, step peroxy acid is added into the water of the extraction system as a 20% w/w to 30% w/w aqueous solution of the peroxy acid.

In one version of the method, the sugar-containing plant material is selected from sugar beet, sugar cane, maize, sorghum, carrots, coconuts, nectarines, pineapples, mangoes, jackfruit, peaches, cantaloupe, apricots, bananas, grapes, apples, pears, cherries, oranges, or any combination thereof. In one version of the method, the sugar-containing plant material is sugar beet.

In one version of the method, the method reduces bacteria count of bacteria that consume sugar. In one version of the method, the method increases yield of sugar from the sugar processing system.

These and other features, aspects, and advantages of the present invention will become better understood upon consideration of the following detailed description, drawings, and appended claims.

DETAILED DESCRIPTION OF THE INVENTION

Figure 1:
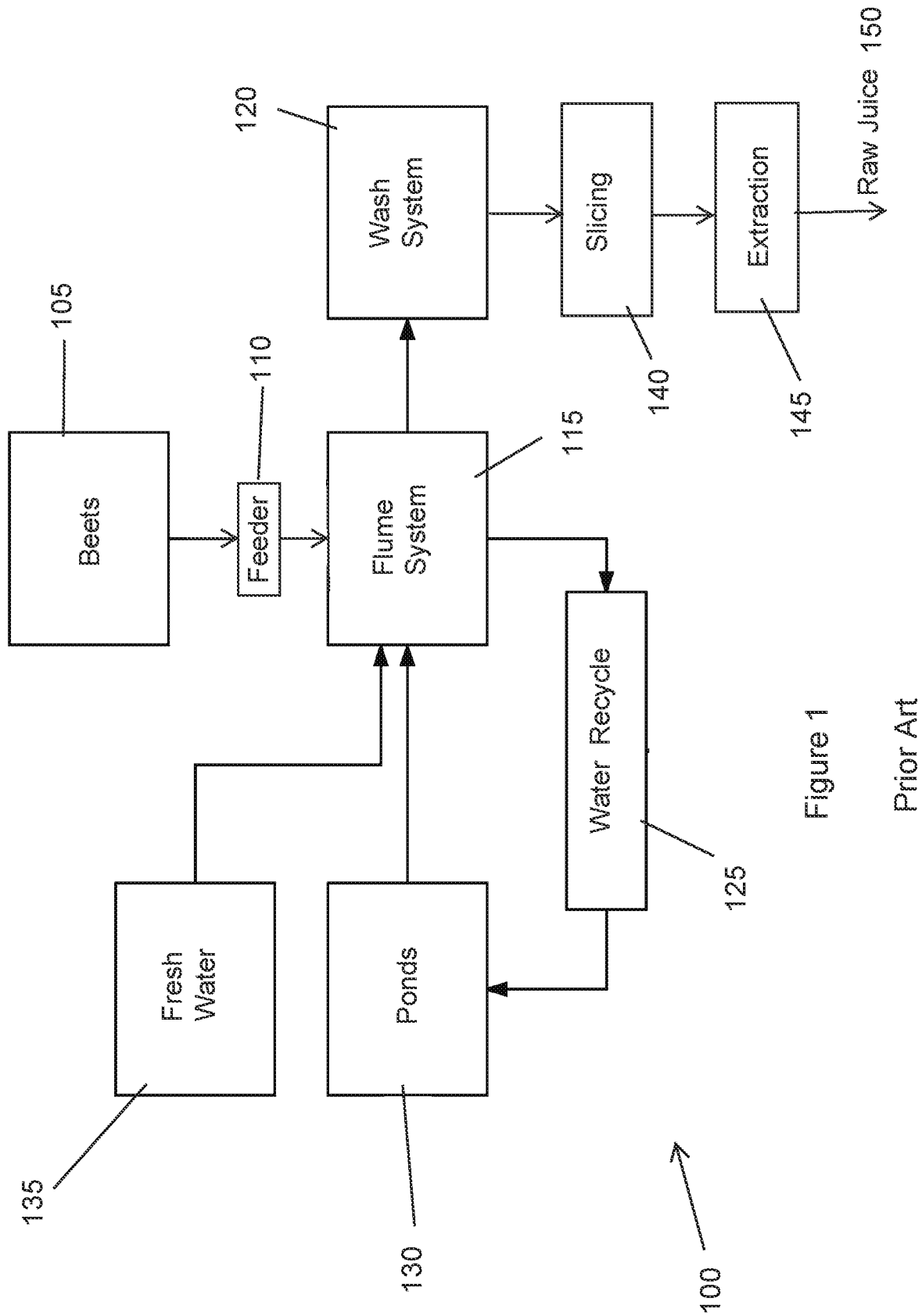
FIG. 1 is a process flow diagram showing part of a prior art beet sugar process.

To provide context for the invention, FIG. 1 shows a diagram of an example part of a prior art beet sugar process 100. Beets 105 from a post-harvest delivery or storage location are transported by a feeder 110, typically a feeder wheel, into a water-containing channel of a flume system 115. A non-limiting example water channel may be 100 feet to 200 feet long and have a transverse cross-section of 3-4 square feet. The water channel of the flume system transports the beets into a beet wash system 120 while simultaneously removing field dirt that might adversely affect slicing and extraction. Water from the flume system is recycled via a water recycle conduit 125 and is then stored in one or more water storage ponds 130, which in a non-limiting example embodiment may be 3-5 acre open air ponds. Some of the water from the pond(s) can be later re-used in the flume system together with optional fresh make-up water 135 for subsequent transport of additional beets. The ponds are typically stagnant water that promotes microbial growth in the absence of chemical treatment. As noted above, acid production is a natural, continuous process in flume-water due to acid-forming bacteria activity. To maintain an acceptable flume water pH in the prior art system of FIG. 1, these acids are neutralized by a prior art alkaline additive, such as lime, to maintain the pH in the alkaline range. Maintaining this high pH controls acid forming bacterial activity.

The wash system washes the beets to remove soil and other external contaminants, and the beets are transported to a mechanical slicing unit 140 that can be used to cut each individual sugar beet into a plurality of thin strips known as "cossettes." The cossettes are then transported to an extraction system 145. Many different machines may be used in the extraction system. The extraction system can comprise placing the cossettes in contact with a counter-current flow of heated water in order to cause the diffusion of sugar-containing materials from the cossettes into the water. The extracted sugar-containing solution exiting the extraction system is referred to as raw juice 150. The raw juice product may be passed through a physical separation apparatus to remove beet juice particles and other suspended solid materials therefrom before further processing of the raw juice. The raw juice can next be purified before sugar crystal production. After the purification, the thin juice is concentrated in an evaporator to provide thick juice. The thick juice is further concentrated by boiling under conditions that allow for crystallization of the sugar.

Figure 2:
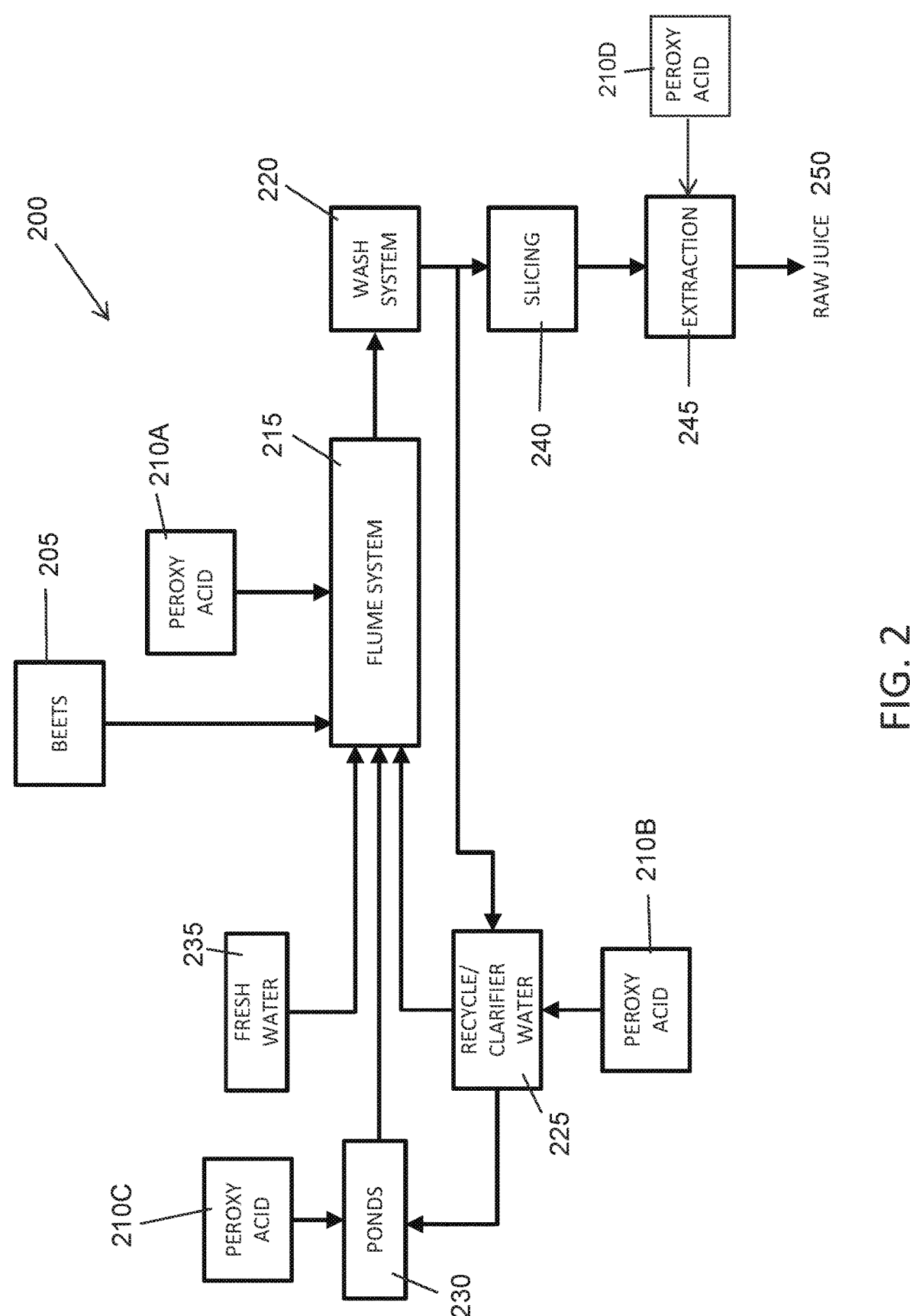
FIG. 2 is a process flow diagram showing one version of a method according to the invention for controlling microbial growth in sugar processing.

Referring now to FIG. 2, there is shown a process flow diagram showing one version of a method 200 according to the invention for controlling microbial growth in sugar processing. In the closed system method 200 of FIG. 2, beets 205 from a post-harvest delivery or storage location are regulated/metered/controlled by a feeder, typically a feeder wheel, into a water-containing channel of a flume system 215. The water channel of the flume system 215 transports the beets 205 into a beet wash system 220. Water from the wash system 220 is recycled to a water recycle/clarifier water unit 225 which may comprise a mechanical and/or chemical settling system. A coagulant may be added to the water recycle/clarifier water unit 225. The treated water from the water recycle/clarifier water unit 225 is transported for storage in one or more water storage ponds 230. Some of the water from the pond(s) 230 can be later re-used in the flume system 215 together with optional treated water from the water recycle/clarifier water unit 225 and optional fresh make-up water 235 for subsequent transport of additional beets 205.

The wash system 220 provides beets to a slicing unit 240 and an extraction system 245 that produces the raw juice 250. The wash system 220 washes the beets to remove soil and other external contaminants, and the beets are transported to the mechanical slicing unit 240 that can be used to cut each individual sugar beet into a plurality of thin strips known as "cossettes." The cossettes are then transported to the extraction system 245. Many different machines may be used in the extraction system 245. The extraction system 245 can comprise placing the cossettes in contact with a counter-current flow of heated water in order to cause the diffusion of sugar-containing materials from the cossettes into the water. The extracted sugar-containing solution exiting the extraction system is referred to as the raw juice 250. The raw juice product may be passed through a physical separation apparatus to remove beet juice particles and other suspended solid materials therefrom before further processing of the raw juice. The raw juice can next be purified before sugar crystal production. After the purification, the thin juice is concentrated in an evaporator to provide thick juice. The thick juice is further concentrated by boiling under conditions that allow for crystallization of the sugar.

In the method 200 of FIG. 2, water in the flume system 215 can be treated with a peroxy acid 210A. The peroxy acid 210A can be added into the water of the flume system 215 at many different addition points. As one non-limiting example, the peroxy acid 210A can be added at a point in the water channel after a beet feeder (e.g., feeder wheel) that is positioned between the delivery or storage location and a water channel of the flume system 215. The beet feeder is a rotating device, similar to an old steamboat's paddle wheel, that is affixed to a structure that allows partial immersion of the beet feeder in the flume and meters the beets as they enter the flume. The beet feeder is typically located near the front of the water flume system, after the beet dump and before weed/rock removal equipment.

In the method 200 of FIG. 2, water in the water recycle/clarifier water unit 225 can be treated with a peroxy acid 210B. In the method 200 of FIG. 2, water in the ponds 230 can be treated with a peroxy acid 210C. In the method 200 of FIG. 2, water in the extraction system 245 can be treated with a peroxy acid 210D.

The treatment of the water in the flume system 215 with peroxy acid 210A, and/or the treatment of the water in the water recycle/clarifier water unit 225 with peroxy acid 210B, and/or the treatment of the water in the ponds 230 with peroxy acid 210C, and/or the treatment of the water in the extraction system 245 with peroxy acid 210D can be continuous, substantially continuous, intermittent, cyclic, batch, or any combination thereof. Treatment can be repeated any desired number of times and treatments can be separated by constant or variable time periods. The rate of addition of a peroxy acid 210A, 210B, 210C, 210D can be constant or variable. A peroxy acid 210A, 210B, 210C, 210D can be added in any manner to the water in the flume system 215, and/or the water recycle/clarifier water unit 225, and/or the pond(s) 230, and/or the extraction system 245, for example, by pouring, by nozzle, by spraying, by misting, by curtain, by weir, by fountain, by percolation, by mixing, by injection, or by any combination thereof.

The peroxy acids 210A, 210B, 210C, 210D used in the method 200 of the invention may be an aqueous solution of a peroxy acid which is ready for use. The peroxy acids 210A, 210B, 210C, 210D can have a formula $R^1CO_3H$, where $R^1$ is selected from $C_1$ to $C_{18}$ alkyl, or the peroxy acids 210A, 210B, 210C, 210D can have a formula $R^1CO_3H$, where $R^1$ is selected from $C_1$ to $C_8$ alkyl. In one non-limiting example embodiment, the peroxy acids 210A, 210B, 210C, 210D each comprise peracetic acid. Each of the peroxy acids 210A, 2106, 210C, 210D may have the same or different formulas, and each of the peroxy acids 210A, 210B, 210C, 210D may be of the same concentration or different concentrations.

In one version of the method 200, the peroxy acid 210A is added into the water of the flume system 215 as a 1% w/w to 35% w/w aqueous solution of the peroxy acid. In another version of the method 200, the peroxy acid 210A is added into the water of the flume system 215 as a 20% w/w to 30% w/w aqueous solution of the peroxy acid 210A.

In one version of the method 200, the peroxy acid 210B is added into the water of the water recycle/clarifier water unit 225 as a 1% w/w to 35% w/w aqueous solution of the peroxy acid 2106. In another version of the method 200, the peroxy acid 2106 is added into the water of the water recycle/clarifier water unit 225 as a 20% w/w to 30% w/w aqueous solution of the peroxy acid 2106.

In one version of the method 200, the peroxy acid 210C is added into the water of the pond(s) 230 as a 1% w/w to 35% w/w aqueous solution of the peroxy acid 210C. In another version of the method 200, the peroxy acid 210C is added into the water of the pond(s) 230 as a 20% w/w to 30% w/w aqueous solution of the peroxy acid 210C.

In one version of the method 200, the peroxy acid 210D is added into the water of the extraction system 245 as a 1% w/w to 35% w/w aqueous solution of the peroxy acid 210C. In another version of the method 200 the peroxy acid 210D is added into the water of the extraction system 245 as a 20% w/w to 30% w/w aqueous solution of the peroxy acid 210C.

Alternatively, the peroxy acids 210A, 210B, 210C, 210D may be prepared by mixing a peroxide source, such as hydrogen peroxide, and an acid which is a precursor of a chosen peroxy acid. The mixing may occur before each of the peroxy acids 210A, 210B, 210C, 210D is added into the water of the flume system 215, and/or the water recycle/ clarifier water unit 225, and/or the pond(s) 230, and/or the extraction system 245, respectively; or the mixing may occur after a peroxide source, such as hydrogen peroxide, and a precursor acid which is a precursor of each of the peroxy acids 210A, 2108, 210C, 210D are added into the water of the water of the flume system 215, and/or the water recycle/clarifier water unit 225, and/or the pond(s) 230, and/or the extraction system 245, respectively. For example, each of the peroxy acids 210A, 210B, 210C, 210D may be prepared by reacting a peroxide source with a carboxylic acid to form the peroxy acid. The peroxide source and the carboxylic acid may be reacted in the water of the flume system 215, and/or the water of the water recycle/clarifier water unit 225, and/or the water of the pond(s) 230, and/or the water in the extraction system 245, respectively. In one non-limiting example embodiment, the peroxide source is hydrogen peroxide, and the carboxylic acid is acetic acid.

In one version of the method 200, the peroxy acid 210A is added into the water of the flume system 215 such that a concentration of the peroxy acid 210A in the water of the flume system 215 is in a range of 1 ppm to 2500 ppm. In one non-limiting example version of the method 200, the peroxy acid 210A is added into the water of the flume system 215 such that a pH in the water of the flume system 215 is in a range of 2 to 12. In another non-limiting example version of the method 200, the peroxy acid 210A is added into the water of the flume system 215 such that a pH in the water of the flume system 215 is in a range of 5.5 to 11. In another non-limiting example version of the method 200, the peroxy acid 210A is added into the water of the flume system 215 such that a pH in the water of the flume system 215 is in a range of 5.5 to 6.9, or in a range of 6.3 to 6.9.

In one version of the method 200, the peroxy acid 210B is added into the water of the water recycle/clarifier water unit 225 such that a concentration of the peroxy acid 2106 in the water of the water recycle/clarifier water unit 225 is in a range of 1 ppm to 2500 ppm. In one non-limiting example version of the method 200, the peroxy acid 210B is added into the water of the water recycle/clarifier water unit 225 such that a pH in the water of the water recycle/clarifier water unit 225 is in a range of 2 to 12. In another non-limiting example version of the method 200, the peroxy acid 210B is added into the water of the water recycle/clarifier water unit 225 such that a pH in the water of the water recycle/clarifier water unit 225 is in a range of 5.5 to 11. In another non-limiting example version of the method 200, the peroxy acid 2106 is added into the water of the water recycle/clarifier water unit 225 such that a pH in the water of the water recycle/clarifier water unit 225 is in a range of 5.5 to 6.9, or in a range of 6.3 to 6.9.

In one version of the method 200, the peroxy acid 210C is added into the water of the ponds(s) 230 such that a concentration of the peroxy acid 210C in the water of the ponds(s) 230 is in a range of 1 ppm to 2500 ppm. In one non-limiting example version of the method 200, the peroxy acid 210C is added into the water of ponds(s) 230 such that a pH in the water of the ponds(s) 230 is in a range of 2 to 12. In another non-limiting example version of the method 200, the peroxy acid 210C is added into the water of the ponds(s) 230 such that a pH in the water of the ponds(s) 230 is in a range of 5.5 to 11. In another non-limiting example version of the method 200, the peroxy acid 210C is added into the water of the ponds(s) 230 such that a pH in the water of the ponds(s) 230 is in a range of 5.5 to 6.9, or in a range of 6.3 to 6.9.

In one version of the method 200, the peroxy acid 210D is added into the water of the extraction system 245 such that a concentration of the peroxy acid 210D in the water of the extraction system 245 is in a range of 1 ppm to 2500 ppm. In one non-limiting example version of the method 200, the peroxy acid 210D is added into the water of the extraction system 245 such that a pH in the water of the extraction system 245 is in a range of 2 to 12. In another non-limiting example version of the method 200, the peroxy acid 210D is added into the water of the extraction system 245 such that a pH in the water of the extraction system 245 is in a range of 5.5 to 11. In another non-limiting example version of the method 200, the peroxy acid 210D is added into the water of the extraction system 245 such that a pH in the water of the extraction system 245 is in a range of 5.5 to 6.9, or in a range of 6.3 to 6.9.

Automated control of the addition of each of the peroxy acids 210A, 2106, 210C, 210D to the water of the flume system 215, and/or the water recycle/clarifier water unit 225, and/or the pond(s) 230, and/or the extraction system 245, respectively, is also possible. A sensor can be placed in each of the water of the flume system 215, and/or the water recycle/clarifier water unit 225, and/or the pond(s) 230, and/or the extraction system 245, respectively, such that fluids passing through the water of the flume system 215, the water recycle/clarifier water unit 225, and/or the pond(s) 230 and/or the extraction system 245 contact the sensor. The sensor measures a physical property of the fluids passing through the water. As used herein, a physical property or a measurable physical property is a property of matter that can be measured or observed without resulting in a change in the composition and identity of a substance. Non-limiting examples of physical properties that can be measured in the sensor include pH, conductivity, oxidation reduction potential, concentration, and density. Sensors are commercially available for measuring these physical properties of the fluids passing through the water channel.

It is contemplated that direct feedback from the sensor can be sent to a programmable logic controller to provide opening and closing times for various valves that control addition of each of the peroxy acids 210A, 2106, 210C, 210D to the water of the flume system 215, and/or the water recycle/clarifier water unit 225, and/or the pond(s) 230 and/or the extraction system 245, respectively. For example, in one version of the method of the invention, the controller can determine a concentration of each of the peroxy acids 210A, 2106, 210C, 210D in the water of the flume system 215, and/or the water recycle/clarifier water unit 225, and/or the pond(s) 230 and/or the extraction system 245, respectively using signal(s) from the sensor, and additional peroxy acid can be added into the water of the flume system 215, and/or the water recycle/clarifier water unit 225, and/or the pond(s) 230, and/or the extraction system 245, respectively by opening a valve when the concentration falls below a predetermined value. In another version of the method of the invention, the sensor is used to sense a measurable physical property (e.g., pH, conductivity, and oxidation reduction potential) of the water of the flume system 215, and/or the water recycle/clarifier water unit 225, and/or the pond(s) 230, and/or the extraction system 245, respectively; the sensor generates a physical property signal corresponding to the measurable physical property wherein the physical property signal correlates to a concentration of the peroxy acid in the water of the flume system 215, and/or the water recycle/clarifier water unit 225, and/or the pond(s) 230, and/or the extraction system 245, respectively; the sensor transmits the physical property signal to the controller; and when the concentration falls below a predetermined value stored in the controller, the controller provides a control signal to open a supply valve in fluid communication with a source of each of the peroxy acids 210A, 210B, 210C, 210D and the water of the flume system 215, and/or the water recycle/clarifier water unit 225, and/or the pond(s) 230, and/or the extraction system 245, respectively thereby adding additional peroxy acid into the water of the flume system 215, and/or the water recycle/clarifier water unit 225, and/or the pond(s) 230, and/or the extraction system 245, respectively.

The method of the invention reduces bacteria count of bacteria that consume sugar. Thus, the method increases yield of sugar from the sugar processing system. Also, the method can reduce a count of insects in the water of the flume system 215, and/or the water recycle/clarifier water unit 225, and/or the pond(s) 230, and/or the extraction system 245. The water of the flume system 215, and/or the water recycle/clarifier water unit 225, and/or the pond(s) 230, and/or the extraction system 245 can be sampled to determine a count of insects and the species of insects in the water, and one can add each of the peroxy acids 210A, 2108, 210C, 210D into the water of the flume system 215, and/or the water recycle/clarifier water unit 225, or the pond(s) 230, and/or the extraction system 245, respectively such that a concentration of each of the peroxy acids 210A, 2108, 210C,

210D in the water of the flume system 215, and/or the water recycle/clarifier water unit 225, and/or the pond(s) 230, and/or the extraction system 245, respectively reduces the count of insects in the water of the flume system 215, and/or the water recycle/clarifier water unit 225, and/or the pond(s) 230, and/or the extraction system 245, respectively.

Thus, the invention provides methods for controlling microbial growth in sugar processing. While a method for controlling microbial growth in a sugar beet processing system is described herein, the sugar-containing plant material may also be selected from sugar cane, maize, sorghum, carrots, coconuts, nectarines, pineapples, mangoes, jackfruit, peaches, cantaloupe, apricots, bananas, grapes, apples, pears, cherries, oranges, or any combination thereof.

Although the present invention has been described in detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A method for controlling microbial growth in a sugar processing system, the method comprising:
 (a) adding a peroxy acid into a water channel of a flume system used for transporting a sugar-containing plant material from a delivery or storage location to a wash system.

2. The method of claim 1 wherein:
 the peroxy acid has a formula $R^1CO_3H$, where $R^1$ is selected from $C_1$ to $C_8$ alkyl.

3. The method of claim 1 wherein:
 the peroxy acid comprises peracetic acid.

4. The method of claim 1 wherein:
 step (a) comprises reacting a peroxide source with a carboxylic acid to form the peroxy acid.

5. The method of claim 1 wherein:
 step (a) comprises adding the peroxy acid into the water channel of the flume system such that a concentration of the peroxy acid in the water of the flume system is in a range of 1 ppm to 2500 ppm.

6. The method of claim 1 wherein:
 step (a) comprises adding the peroxy acid into the water channel of the flume system such that a pH in the water of the flume system is in a range of 5.5 to 6.9.

7. The method of 1 further comprising:
 (b) sensing a measurable physical property of the water of the flume system;
 (c) generating a physical property signal corresponding to the measurable physical property, the physical property signal correlating to a concentration of the peroxy acid in the water of the flume system;
 (d) transmitting the physical property signal to a controller; and
 (e) when the concentration falls below a predetermined value stored in the controller, providing a control signal from the controller to open a supply valve in fluid communication with a source of the peroxy acid and the flume system thereby adding additional peroxy acid into the water channel of the flume system.

8. The method of claim 7 wherein:
 the measurable physical property is selected from the group consisting of pH, conductivity, and oxidation reduction potential.

9. The method of claim 1 wherein:

step (a) comprises adding the peroxy acid into the water channel of the flume system at a point after a beet feeder that is positioned between the delivery or storage location and a water channel of the flume system.

10. The method of claim 1 wherein:

the peroxy acid is added into the water channel of the flume system as a 1% w/w to 35% w/w aqueous solution of the peroxy acid.

11. The method of claim 1 wherein:

the peroxy acid is added into the water channel of the flume system as a 20% w/w to 30% w/w aqueous solution of the peroxy acid.

12. The method of claim 1 wherein:

the sugar-containing plant material is sugar beet.

13. The method of claim 1 wherein:

step (a) comprises sampling the water of the flume system to determine a count of insects in the water of the flume system and adding the peroxy acid into the water channel of the flume system such that a concentration of the peroxy acid in the water of the flume system reduces the count of insects in the water of the flume system.

14. The method claim 1 further comprising:

(b) adding additional peroxy acid into a recycled water unit that is in fluid communication with (i) a water storage pond and (ii) an outlet of the wash system or an outlet of the flume system.

15. The method claim 1 further comprising:

adding additional peroxy acid into a water storage pond that is in fluid (b) communication with an inlet of the flume system.

16. The method claim 1 further comprising:

(b) adding additional peroxy acid into water of an extraction system of the sugar processing system.

17. A method for controlling microbial growth in a sugar processing system having a flume system used for transporting a sugar-containing plant material from a delivery or storage location to a wash system wherein lime is used in the flume system, the method comprising:

(a) replacing at least a portion of the lime with a peroxy acid, wherein the peroxy acid is added into a water channel of the flume system.

18. The method of claim 17 wherein:

the peroxy acid has a formula $R^1CO_3H$, where $R^1$ is selected from $C_1$ to $C_8$ alkyl.

19. The method of claim 17 wherein:

the peroxy acid comprises peracetic acid.

\* \* \* \* \*